United States Patent [19]

Smith et al.

[11] Patent Number: 6,155,812
[45] Date of Patent: Dec. 5, 2000

[54] CEMENT MOLD FOR A TEMPORARY IMPLANT

[75] Inventors: Daniel Bryce Smith, Warsaw; Mark V. Vandewalle, Pierceton, both of Ind.; Frank Ebert, Baltimore, Md.

[73] Assignee: Biomet, Inc, Warsaw, Ind.

[21] Appl. No.: 09/116,109

[22] Filed: Jul. 15, 1998

[51] Int. Cl.[7] .......................... B29C 33/10; B29C 33/42; B29C 43/02
[52] U.S. Cl. .............................. 425/318; 249/55; 249/61; 249/141; 249/168; 623/901
[58] Field of Search ............................... 249/55, 61, 168, 249/141; 425/2, 116, 117, 318; 623/901

[56] References Cited

U.S. PATENT DOCUMENTS

| | | | |
|---|---|---|---|
| 1,525,126 | 2/1925 | Goldstein | 249/141 |
| 2,347,567 | 4/1944 | Kresse . | |
| 3,014,614 | 12/1961 | Carroll et al. | 249/61 |
| 3,580,484 | 5/1971 | Schneider | 249/61 |
| 3,774,244 | 11/1973 | Walker . | |
| 3,857,932 | 12/1974 | Shepherd et al. . | |

(List continued on next page.)

FOREIGN PATENT DOCUMENTS

| | | |
|---|---|---|
| 0 016 480 A1 | 10/1980 | European Pat. Off. . |
| 0 129 531 A2 | 12/1984 | European Pat. Off. . |
| 2 639 820 | 6/1990 | France . |
| 297 03 971 U | 9/1998 | Germany . |

OTHER PUBLICATIONS

Wilde & Ruth, "Two Stage Reimplantation in Infected Total Knee Arthroplasty"; Clinical Orthopaedics & Related Research, No. 236, Nov., 1998; pp. 23–35.

Hofmann, Kane, Tkach, Plaster, & Camargo; Clinical Orthopaedics & Related Research, "Treatment of Infected Total Knee Arthroplasty Using an Articulating Spacer"; Clinical Orthopaedics and Related Research; ©1995 Lippincott–Raven Publishers; No. 321, pp. 45–54.

Goodell, Flick, Hebert & Howe, "Preparation and Release Characteristics of Tobramycin–impregnated Polymethylmethacrylate Beads"; American Journal of Hospital Pharmacy, vol. 43, Jun., 1986; pp. 1454–1451.

Flick, Herbert, Goodell, & Kristiansen; Clinical Orthopedics & Related Research, "Noncommercial Fabrication of Antibiotic–impregnated Polymethylmethacrylate Beads"; No. 223, Oct. 1987, pp. 282–286.

Cohen, Hozack, Cuckler, Booth, "Two–Stage Reimplantation of Septic Total Knee Arthroplasty"; The Journal of Arthroplasty, vol. 3, No. 4, Dec., 1988; pp. 369–377.

Booth Jr & Lotke, "The Results of Spacer Block Technique in Revision of Infected Total Knee Arthroplasty", Clinical Orthopaedics and Related Research No. 248, Nov., 1989; pp. 57–60.

*Primary Examiner*—Robert Davis
*Attorney, Agent, or Firm*—Harness, Dickey & Pierce, P.L.C.

[57] ABSTRACT

A cement mold for use in forming a temporary orthopedic implant used in an orthopedic surgical procedure. The cement mold includes a first mold to define a first portion of the temporary implant and a second mold to define a second portion of the temporary implant. A coupling mechanism joins the first mold to the second mold such that the cement mold is substantially sealed to define the temporary implant. The cement mold further defines an input port which is operable to receive a delivery nozzle to supply antibiotic loaded bone cement within an inner sidewall of the cement mold. At least one ventilation port is defined by the cement mold which is operable to vent trapped air upon filling the cement mold with the antibiotic loaded bone cement through the input port. The cement mold further includes a removal mechanism which is operable to assist in tearing and separating the cement mold from the temporary implant.

21 Claims, 5 Drawing Sheets

U.S. PATENT DOCUMENTS

| | | | |
|---|---|---|---|
| 3,882,858 | 5/1975 | Klemm . | |
| 3,907,245 | 9/1975 | Linder | 249/168 |
| 3,964,106 | 6/1976 | Hutter, Jr. et al. . | |
| 3,966,166 | 6/1976 | Elliot | 249/55 |
| 4,059,684 | 11/1977 | Gross et al. . | |
| 4,191,740 | 3/1980 | Heusser et al. . | |
| 4,322,398 | 3/1982 | Reiner et al. | 424/19 |
| 4,375,810 | 3/1983 | Belykh et al. | 128/92 R |
| 4,550,723 | 11/1985 | Belykh et al. | 623/16 |
| 4,581,028 | 4/1986 | Fox, Jr. et al. | 623/2 |
| 4,610,692 | 9/1986 | Eitenmuller et al. | 623/16 |
| 4,615,705 | 10/1986 | Scales et al. | 623/11 |
| 4,624,673 | 11/1986 | Meyer | 623/16 |
| 4,739,963 | 4/1988 | Parmacek et al. | 249/61 |
| 4,749,585 | 6/1988 | Greco et al. | 427/2 |
| 4,750,905 | 6/1988 | Koeneman et al. | 623/16 |
| 4,797,282 | 1/1989 | Wahlig et al. | 424/422 |
| 4,853,225 | 8/1989 | Wahlig et al. | 424/423 |
| 4,869,906 | 9/1989 | Dingeldein et al. | 424/423 |
| 4,882,149 | 11/1989 | Spector | 424/425 |
| 4,888,024 | 12/1989 | Powlan | 623/23 |
| 4,900,546 | 2/1990 | Posey-Dowty et al. | 623/16 |
| 4,917,589 | 4/1990 | Manderson | 425/318 |
| 4,919,666 | 4/1990 | Buchhorn et al. | 623/16 |
| 4,950,300 | 8/1990 | Langlais | 623/23 |
| 5,015,257 | 5/1991 | Crowninshield et al. | 623/22 |
| 5,033,712 | 7/1991 | Ravet | 249/61 |
| 5,061,286 | 10/1991 | Lyle | 623/16 |
| 5,098,620 | 3/1992 | Bradley et al. | 264/313 |
| 5,123,927 | 6/1992 | Duncan et al. | 623/20 |
| 5,133,771 | 7/1992 | Duncan et al. | 623/23 |
| 5,141,521 | 8/1992 | Wenner | 623/901 |
| 5,236,457 | 8/1993 | Devanathan | 623/901 |
| 5,501,687 | 3/1996 | Willert et al. | 606/94 |
| 5,538,514 | 7/1996 | Hawkins | 623/16 |

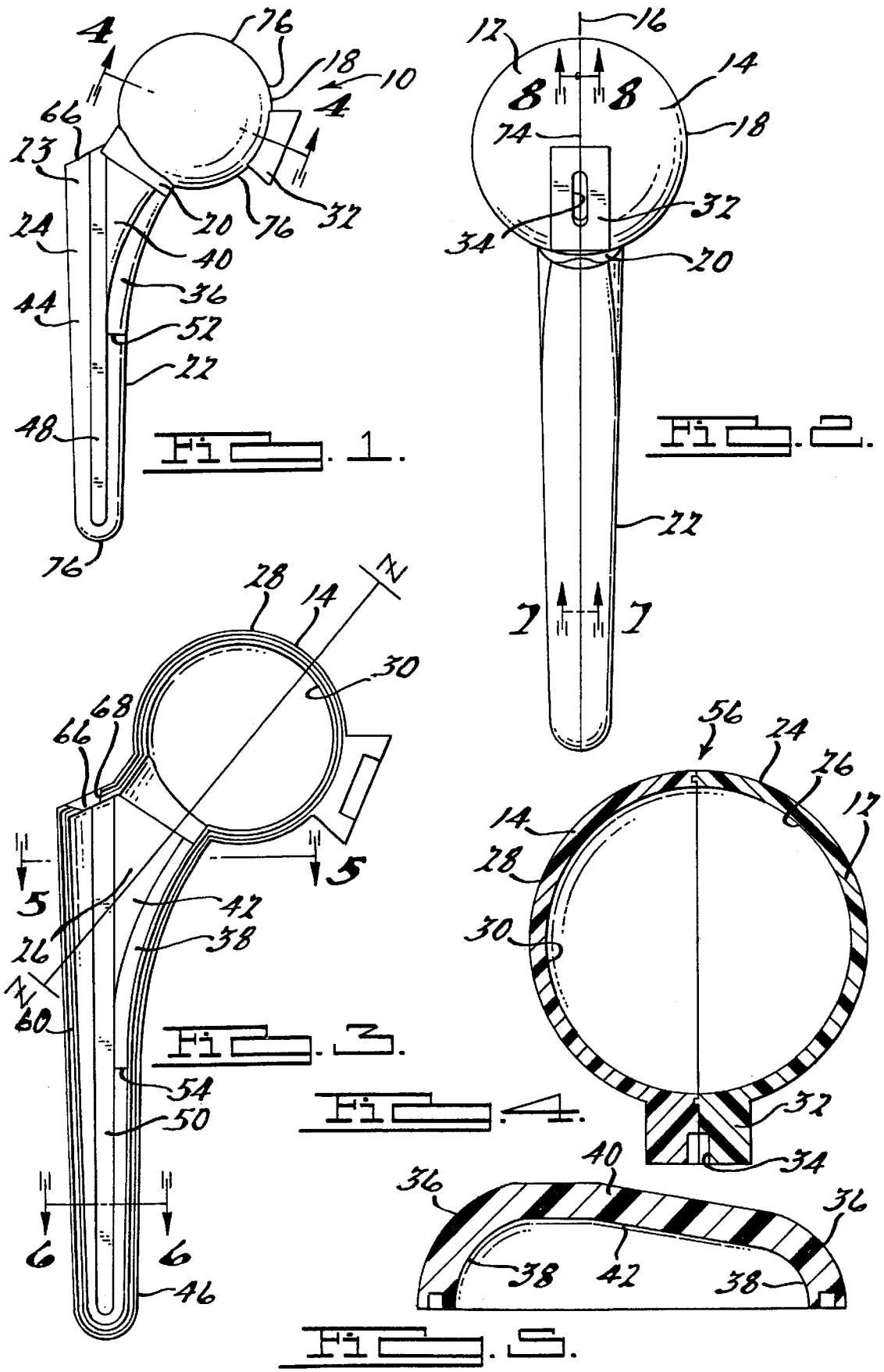

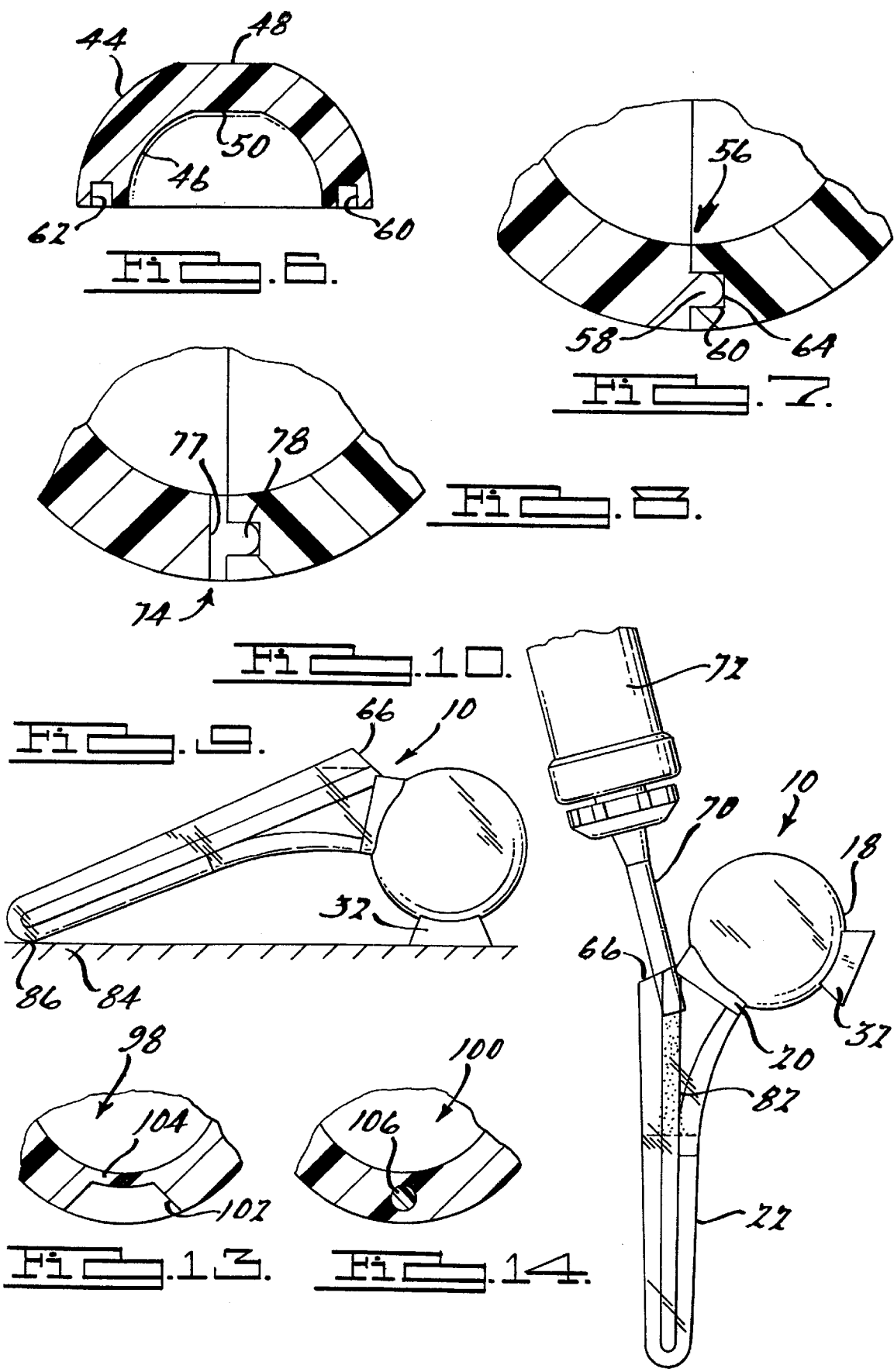

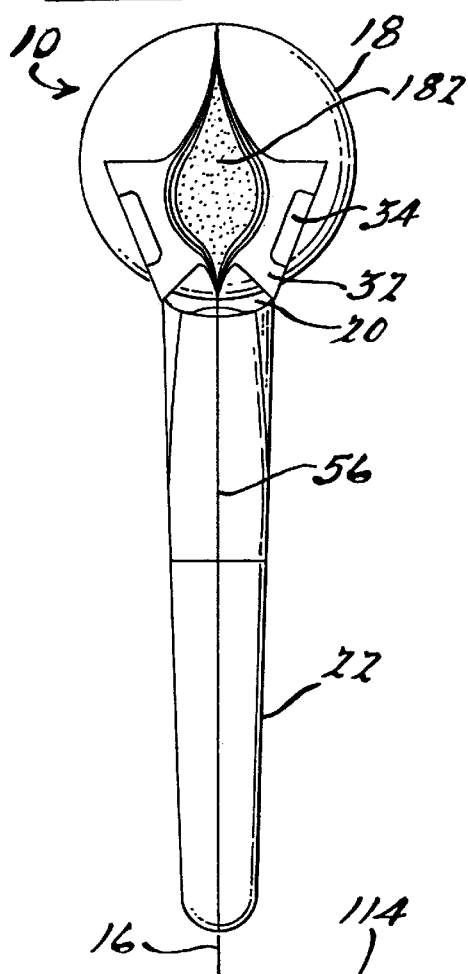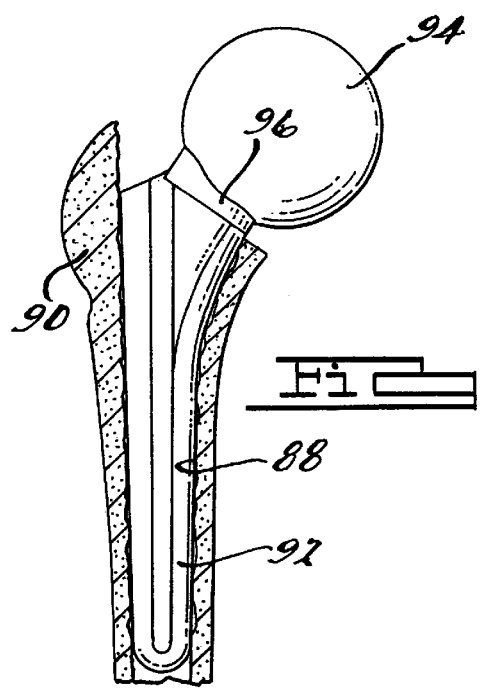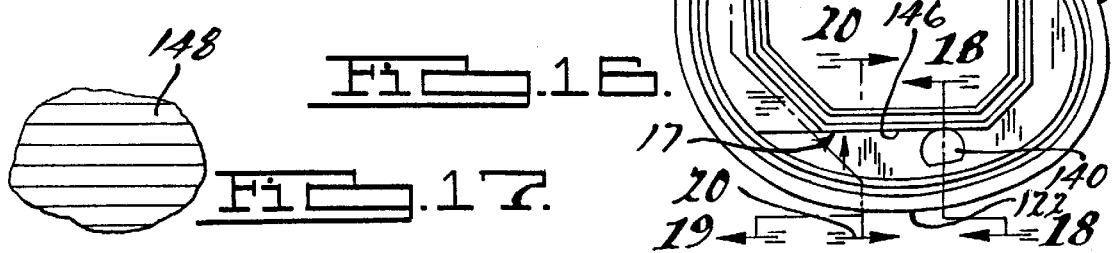

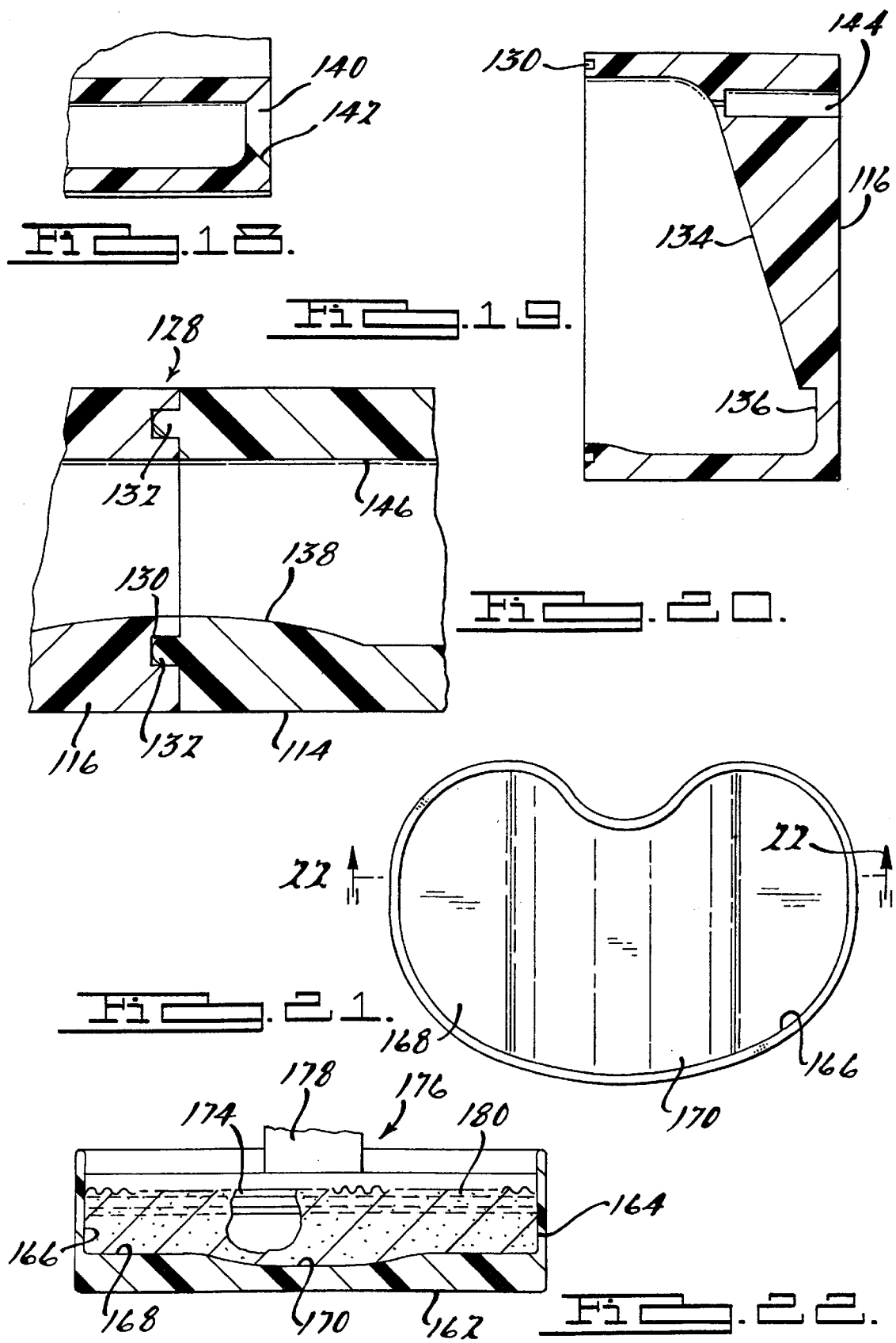

CEMENT MOLD FOR A TEMPORARY IMPLANT

BACKGROUND OF THE INVENTION

1. Field of the Invention

This invention relates generally to orthopedic implants for use in orthopedic surgical. procedures and, more particularly, to cement molds for use in forming temporary orthopedic implants used in orthopedic surgical procedures.

2. Discussion of the Related Art

A natural joint may undergo degenerative changes due to a variety of etiologies. When these degenerative changes become so far advanced and irreversible, it may ultimately become necessary to replace the natural joint with a joint prosthesis. However, due to any number of reasons, a small portion of patients that undergo such orthopedic surgical procedures suffer from infections at the surgical site and generally around the implanted joint prosthesis. In order to cure such an infection in a two-stage reimplantation, the implanted joint prosthesis is generally removed, the site is thoroughly debrided and washed, antibiotics are applied to the infected site until the infection is eliminated, and a new revision type joint prosthesis is then implanted during a subsequent orthopedic surgical procedure. Systemic antibiotics may also act as an adjunct to local antibiotic delivery. Another technique, more popular in Europe, is the one stage reimplantation in which the prosthesis is removed, the site is debrided and washed and a new permanent implant is cemented in place using antibiotic loaded bone cement.

The currently available techniques for delivering the antibiotic to the infected joint area include mixing appropriate bone cement, such as (PMMA) poly-methylmethacrylate, with an antibiotic, such as gentamicin, and applying the mixture to the infected joint area. Another technique involves the use of pre-loaded antibiotic cement beads which are retained on a string or wire. The antibiotic loaded bone cement is packed into the voids created by the explanted joint prosthesis while the joint is distended or the string of antibiotic loaded beads are dropped into the respective voids. During this period, the antibiotic leaches out from the bone cement and into the infected area, while the patient is unfortunately left substantially non-ambulatory or bedridden with very limited mobility. In addition, soft tissue contraction in the area about the joint may cause a more difficult revision surgery since the remaining bone portion is smaller than the explanted joint prosthesis. Moreover, the above techniques may also suffer from the disadvantage of sometimes being difficult or messy to use during the orthopedic surgical procedure. This disadvantage is primarily exhibited during the use of the antibiotic loaded bone cement in a doughy state and attempting to fill the appropriate region in the distended joint area.

In order to improve upon this technique, other techniques have involved the use of partial molds or casts in which the mixture of bone cement and antibiotic is packed into these partial molds by use of spoons or spatulas and left to harden. Once hardened, the brittle molds may be broken away and the bone cement, now resembling a joint prosthesis, is applied to the appropriate joint area. However, this technique also suffers from several disadvantages in that the partial molds or casts are made from a brittle material such that the molds are prone to fracturing or breaking before their use. Moreover, the molds are only partial molds in that only portions of the implant are formed and the molds generally have large exposed cavities such as two ends of a tube to receive the bone cement. This makes it extremely difficult to pack or load such molds with the antibiotic loaded bone cement. Furthermore, it is often times difficult to break away or remove these molds from the hardened bone cement.

Such disadvantages are also exhibited in U.S. Pat. Nos. 5,123,927 and 5,133,771 to Duncan, et al. in which a knee prosthesis and a hip prosthesis technique are disclosed. Here again, the disadvantages associated with the '927 and '771 patents are that they are somewhat clumsy and messy to work with. In other words, both the '927 and the '771 patents provide partial molds that are substantially open such that a rigid or hard bearing member is separately implanted into each of the molds to provide for an articulating temporary joint. Here again, however, the molds are filled manually by the use of spoons, spatulas, etc. and the molds do not provide a means for readily removing the molds once the antibiotic impregnated bone cement hardens. In addition, it appears that these molds are also reusable which requires the molds to be cleaned and sterilized before each use.

What is needed then is a cement mold to form a temporary implant which does not suffer from the above mentioned disadvantages. This, in turn, will provide a substantially completely sealed mold which may be filled in an automatic or controlled matter, provide a mold which may be readily handled and easily removed from the hardened bone cement, provide a mold that is easily tearable, provide a means to easily remove the mold from the formed temporary implant, reduce the amount of time a patient is bedridden, increase the efficiency of the surgical procedure while reducing the surgical time and cost, eliminating any recleaning or resterilizing, and create a repeatable procedure by providing a substantially fully enclosed and complete mold. It is, therefore, an object of the present invention to provide such a cement mold to form a temporary implant for use during an orthopedic surgical procedure.

SUMMARY OF THE INVENTION

In accordance with teachings of the present invention, a cement mold for use in forming a temporary orthopedic implant used in an orthopedic surgical procedure is disclosed. This is basically achieved by providing an improved cement mold which is substantially sealed except for an input port and ventilation ports, as well as having a removal mechanism operable to assist in separating the cement mold from the temporary implant.

In one preferred embodiment, a cement mold to form a temporary implant for use in delivering antibiotics to an infected site includes a first mold and a second mold. The first mold defines a first portion of the temporary implant and the second mold defines a second portion of the temporary implant. A coupling mechanism joins the first mold to the second mold such that the cement mold is substantially sealed to define the temporary implant.

In another preferred embodiment, a cement mold to form a temporary implant for use in delivering antibiotics to an infected site includes an outer sidewall and an inner sidewall where the inner sidewall defines the shape of the temporary implant. An input port is defined by the cement mold and is operable to receive a delivery nozzle to supply antibiotic loaded bone cement within the inner sidewall. At least one ventilation port is defined by the cement mold and is operable to vent trapped air upon filling the cement mold with the antibiotic loaded bone cement through the input port.

In yet another preferred embodiment, a cement mold to form a temporary implant for use in delivering antibiotics to an infected site includes an outer sidewall and an inner sidewall where the inner sidewall defines the shape of the temporary implant. A removal mechanism forming a portion of the cement mold is operable to assist in separating the cement mold from the temporary implant.

Use of the present invention provides a cement mold for use in forming a temporary orthopedic implant used in orthopedic surgical procedures. As a result, the aforementioned disadvantages associated with the currently available methods and techniques for delivering antibiotics to an infected site have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a side elevational view of a cement mold for a temporary hip implant according to the teachings of a first preferred embodiment of the present invention;

FIG. 2 is a front elevational view of the cement mold of FIG. 1;

FIG. 3 is a side internal elevational view of one-half of the cement mold of FIG. 1;

FIG. 4 is a cross-sectional view of the cement mold of FIG. 1 taken along line 4—4 of FIG. 1;

FIG. 5 is a cross-sectional view of the cement mold of FIG. 1 taken along line 5—5 of FIG. 3;

FIG. 6 is a cross-sectional view of the cement mold of FIG. 1 taken along line 6—6 of FIG. 3;

FIG. 7 is an enlarged cross-sectional view of a joint for the cement mold of FIG. 1 taken along line 7—7 of FIG. 2;

FIG. 8 is an enlarged cross-sectional view of a vent for the cement mold of FIG. 1 taken along line 8—8 of FIG. 2;

FIGS. 9–12 illustrate a method for filling and implanting the hip implant formed from the cement mold of FIG. 1 according to the teachings of the first preferred embodiment of the present invention;

FIG. 13 is a side cross-sectional view of a first removal mechanism for removing the cement mold of FIG. 1;

FIG. 14 is a side cross-sectional view of a second removal mechanism for removing the cement mold of FIG. 1;

FIG. 15 is a perspective view of a cement mold for a temporary femoral knee implant according to the teachings of a second preferred embodiment of the present invention;

FIG. 16 is a side interior elevational view of one-half of the cement mold of FIG. 15;

FIG. 17 is an interior view of a surface texture of the cement mold of FIG. 15 taken about arrow 17 of FIG. 16;

FIG. 18 is a cross-sectional view of the cement mold of FIG. 15 taken about line 18—18 of FIG. 16;

FIG. 19 is a cross-sectional view of the cement mold of FIG. 15 taken about line 19—19 of FIG. 16;

FIG. 20 is a cross-sectional view of the assembled cement mold taken relative to line 20—20 of FIG. 16;

FIG. 21 is a top elevational view of a cement mold for a temporary tibial knee implant according to the teachings of a third preferred embodiment of the present invention;

FIG. 22 is a side cross-sectional view of the cement mold of FIG. 21 taken along line 22—22 and including a forming paddle;

DETAILED DESCRIPTION OF THE PREFERRED EMBODIMENT(S)

Figure 23:
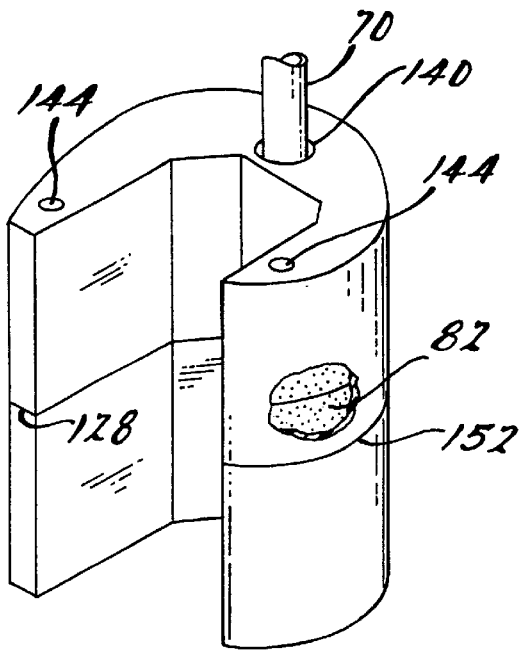
FIGS. 23–24 illustrate a method for filling and implanting the femoral and tibial knee implants formed by the cement molds of FIGS. 15 and 21.

The following description of the preferred embodiments concerning cement molds for temporary implants used during orthopedic surgical procedures are merely exemplary in nature and are not intended to limit the invention or its application or uses. Moreover, while the present invention is described in detail below with reference to cement molds for hip and knee joints, it would be appreciated by those skilled in the art the present invention is clearly not limited to only cement molds for hip and knee joints but may be utilized at various other areas for various other orthopedic surgical procedures.

Referring to FIGS. 1–2, a cement mold 10 according to the teachings of the first preferred embodiment of the present invention is shown. The cement mold 10 is used to form a temporary femoral hip implant or prosthesis to replace a right of left portion of a femoral hip joint for a temporary healing period. The cement mold 10 is preferably formed from silicone having the properties of being translucent, as well as readily tearable. The silicone selected should also have a sufficiently high stiffness such that the cement mold 10 will not sag or be deformed upon handling. The preferred silicone that achieves these characteristics is Dow Q7-4780 or any other 80 durometer silicone. Moreover, it should be noted that the material selected must also not adversely react with the bone cement and antibiotic selected. The cement mold 10 may of course be made of any other material which exhibit similar properties.

The cement mold 10 includes a first half 12 and a second half 14 which are joined along substantially the coronal plane 16 of the subsequently formed temporary femoral hip implant. Each half 12 and 14 include an articulating head portion 18, an enlarged neck portion 20 and an elongated stem portion 22.

Each of these portions 18–22 will now be discussed with reference to the first half 12 with the understanding that the first half 12 and the second half 14 are essentially mirror images of one another and like reference numerals will be used to identify like structures for each half.

The first half 12 of the cement mold 10 includes an outer sidewall 24 and an inner sidewall 26 which defines the entire shape of the temporary implant. Specifically, the head portion 18 includes an outer hemispherical sidewall 28 and an inner hemispherical sidewall 30 used to form a substantially spherical articulating head. The head portion 18 further includes a trapezoidal shaped foot 32 having a cutout region 34, further discussed herein. The neck portion 20 is enlarged to provide additional strength for the temporary implant. The proximal stem portion 23 includes outer arcuate sidewalls 36 and inner arcuate sidewalls 38 with a substantially triangular shaped planer outer sidewall 40 and inner sidewall 42. The distal stem portion 22 includes an outer arcuate sidewall 44 and an inner arcuate sidewall 46 and an outer elongated planer sidewall 48 and an inner elongated planer sidewall 50. Located at about the midpoint of the elongated stem portion 22 is an outer transverse transition area 52 and an inner transverse transition area 54.

The first half 12 and the second half 14 of the cement mold 10 are separately molded by various conventional molding techniques such as injection molding, compression molding, blow molding, spin casting, etc. The first half 12 and the second half 14 are joined substantially along the coronal plane 16 by means of a connecting or coupling mechanism 56. The coupling mechanism 56 is essentially a tongue and groove coupling mechanism 56 having a substantially rounded tongue 58 running about the outer circumference along the coronal plane 16 of the first half 12. A rectangular groove 60 is positioned also substantially around the outer circumference of the second half 14 along the coronal plane 16. The tongue 58 is rounded to provide a self centering mechanism and also to assist in engaging the rounded tongue 58 within the rectangular shaped groove 60 since engaged silicone does not slide readily with respect to one another. The tongue 58 is adhered to the groove 60 by use of a silicone adhesive that is generally applied to only the inner sidewalls 62 of the rectangular groove 60 and/or the outer sidewalls 64 of the rounded tongue 58. In this way, separation and tearing of the first half 12 from the second half 14 generally occurs along the coronal plane 16 further discussed herein. It should also be noted that any other type of coupling mechanism could also be employed such as two planar surfaces adhered together, differently shaped mating surfaces, etc.

Since the fully assembled cement mold 10 creates a substantially completely enclosed cement mold 10, an input port 66 is formed into the proximal stem portion 23 of both the first half 12 and the second half 14. The input port 66 is defined by a tapered sidewall 68 and is flexible enough to sealably receive a delivery nozzle 70 of a conventional cement gun 72. Since the nozzle 70 will generally seal the input port 66, a plurality of vent holes 74 are formed about the cement mold 10. Specifically, a vent hole 74 is located at the distal end of the elongated stem portion 22 and three vent holes 74 are positioned substantially uniformly about the circumference or outer parameter of the head portion 18, each identified by reference numeral 76 in FIG. 1. The vents 74 are formed substantially along the coronal plane 16 and are defined through the tongue and groove coupling mechanism 56. Specifically, upon review of FIG. 10, the vent 74 is essentially defined by a first laterally extending planer sidewall 77 and a pair of opposed laterally extending sidewalls 78 which essentially removes a portion of the tongue 58.

The procedure for using the cement mold 10 to form a temporary femoral hip prosthesis 80 will now be described with reference to FIGS. 9–12. First, a surgeon or assistant will generally mix the appropriate bone cement with the appropriate antibiotic. For example, in many instances, about two grams of antibiotic are mixed with each 40 gram packet of bone cement powder which is then mixed with a corresponding number of 20 milliliter ampoules of a liquid monomer. The bone cement may be a poly-methylmethacrylate (PMMA) cement such as that produced under the trade names CMW1, CMW2, CMW3, Zimmer Dough Type, or Zimmer LVC, or a MMA-styrene copolymer cement such as that produced under the trade names Howmedia Simplex P or Zimmer Osteobond, or an MMA-methyl acrylate copolymer such as that produced under tradename Palacos R while the antibiotic may be a gentamicin or any other appropriate antibiotic. Once the appropriate antibiotic loaded bone cement 82 is mixed, the bone cement 82 is put within a cement delivery gun 72.

With the cement gun 72 loaded with the bone cement 82, an appropriately sized cement mold 10 which comes preassembled, will be selected. The cement molds 10 will be supplied in an array of sizes to meet various patient's needs.

Once the appropriately sized cement mold 10 is selected, a surgeon will generally grasp the cement mold 10 and slidably and sealably insert the nozzle 70 into the input port 66. With the nozzle 70 substantially sealing the input port 66, the surgeon will engage the cement gun 72 to pump out the bone cement 82 within the inner sidewall 26 of the cement mold 10. As the bone cement 82 is delivered within the mold 10, air trapped within the cement mold 10 is released, via the four vent holes 74, which are positioned at various extreme points in the cement mold 10. Since the input port 66 is somewhat flexible, the surgeon may direct or angle the nozzle 70 within the cement mold 10 to insure that the cement mold is fully filled with the bone cement 82. Moreover, with the silicone being somewhat transparent, this enables the surgeon to determine that the cement mold 10 has been fully filled without substantially any air pockets or voids.

Once the cement mold 10 is filled by the cement gun 72, the cement mold 10 may be placed on a surgical table 84 with the foot 32 and a distal end or point 86 contacting the surgical table 84. In this way, the surgeon may set the filled cement mold 10 down to let the bone cement 82 cure while the surgeon moves on to another task, thereby substantially increasing the efficiency and reducing the time for the surgical procedure. Once the bone cement 82 has sufficiently cured, the surgeon may simply grasp the cement mold 10 with the foot 32 facing the surgeon, as shown in FIG. 11. The surgeon can then slip his or her thumbs within the cutout region 34 since the first half 12 and the second half 14 are simply adhered along the tongue and groove coupling mechanism 56. This enables the foot 32 to be substantially separated along the coronal plane 16 up to the tongue and groove coupling mechanism 56. Since the silicone has a tear characteristic, by applying a sufficient separating force, the cement mold 10 will substantially separate and tear along the coronal plane 16 as shown in FIG. 11. Should it be desired to provide further assistance in this tearing, a surgeon can simply score the coupling mechanism 56 about the circumference of the cement mold 10 along the coronal plane 16 with a scalpel.

The temporary hip implant or prosthesis 80 formed from the antibiotic loaded bone cement 82 may then be simply engaged in the intramedullary canal 88 of the host femur 90, as shown in FIG. 12. The distal stem 92 of the implant 80 is snugly fit within the intramedullary canal 88 while an articulating head 94 coupled to a neck 96 is rotatably engaged with the acetabulum. This will enable the distended joint to be subsequently re-engaged with the temporary implant 80 to enable limited non-load bearing movement by the patient. This will enable the patient to generally sit up or be transported out of a hospital during the temporary recovery stage prior to having a revision type prosthesis subsequently implanted. During this time the antibiotic in the bone cement 82 leaches out over time to the infected area and soft-tissue tension is maintained.

Turning to FIGS. 13–14, a first removal mechanism 98 and a second removal mechanism 100 are shown, respectively. The first removal mechanism 98 is essentially defined by a tapered sidewall 102 which forms a substantially thinned sidewall or member 104 located on the inner sidewall 26. The thinned sidewall 104 is located on the inner sidewall 26 such that the prosthesis 80 will be substantially smooth and not have any voids or grooves passing therethrough. The thinned sidewall 104 may assist in the tearing of the cement mold 10 along this region. The thinned sidewall 104 may run substantially about the circumference of the cement mold 10 along the coronal plane 16 or run substantially about the circumference of head portion 18 and proximal stem portion 23 along plane Z—Z. The thinned sidewall 104 can also run along any other desired area so that the cement mold 10 may be separated and torn in multiple pieces. The thinned sidewall 104 may have an extending tab which enables the surgeon to grasp the tab and initiate the tearing.

Turning to FIG. 14, the second removal mechanism 100 consists of an embedded line or string 106 which is substantially embedded between the outer sidewall 24 and the inner sidewall 26. The embedded line 106 will be routed along the cement mold 10 similar to the thinned sidewall 104 with a portion of the line 106 extending out of the cement mold 10 which is operable to be grasped by the surgeon. Upon grasping the line 106, the surgeon may simply pull on the line 106 to tear away at the mold 10, thereby easily exposing the implant 80.

Turning now to FIGS. 15–24, a cement mold 110 used to fabricate a temporary femoral knee implant and a cement mold 112 used to fabricate a temporary tibial knee implant are shown. The cement mold 110 for the femoral knee implant includes a first half 114 and a second half 116 to provide a substantially sealed and complete mold. Here again, the first half 114 and the second half 116 are essentially mirror images of one another except for the location of an input port and venting holes further discussed herein. As such, like reference numerals will be used to identify like structures for each half 114 and 116, respectively. The cement mold 110 includes an anterior portion 118, a posterior portion 120 and a distal portion 122 formed therebetween to substantially form two condyles of the temporary femoral knee implant. The cement mold 110 includes an outer sidewall 124 and an inner sidewall 126 which defines the temporary femoral knee implant. Here again, the first half 114 and the second half 116 are joined together by a tongue and groove coupling mechanism 128, shown clearly in FIG. 20 or any other coupling mechanism. The tongue and groove coupling mechanism 128 includes a rectangular groove 130 within the second half 116 and a rounded tongue 132 within the first half 114.

The anterior portion 118 is tapered inward along an interior sidewall 134, as shown in FIG. 19 which widens at the distal portion 122 at sidewall 136. The posterior portion 120 is not tapered and substantially extends along the plane of the sidewall 136. Running along the distal portion 122 is an arcuate shaped sidewall 138 which defines the two condyles of the femoral knee prosthesis. Since the cement mold 110 is substantially sealed, an input port 140 passes through the second half 116 near the distal portion 122. The input port 140 is defined by tapered sidewall 142 which enables the nozzle 70 of the cement gun 72 to be slidably and sealably received within the input port 140.

In order to vent the substantially sealed and complete cement mold 110, a pair of ventilation holes or ports 144 are provided in the anterior portion 118 and the posterior portion 120 of the second half 116 (see FIG. 16). The vents 144 pass through the sidewall 134, as shown in FIG. 19, to vent the interior region as it is filled with bone cement. The inner sidewall 146 which faces the femur is also formed with a plurality of ridges 148, as shown in FIG. 17, to provide additional surface area for leaching of the antibiotic, as well as a textured surface to engage the femur. It should further be noted that the ridges 148 or any other texture may also be applied to any of the appropriate inside surfaces of any of the cement molds discussed herein.

Figure 24:
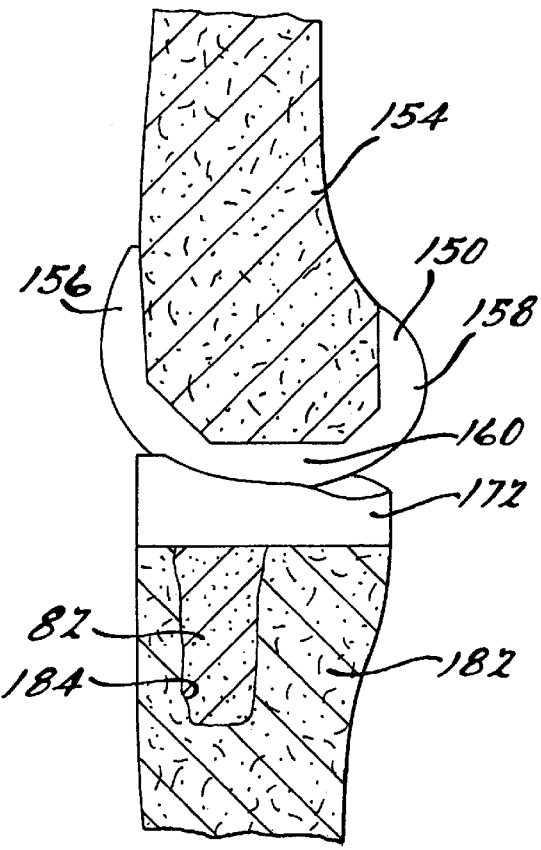

Turning now to FIGS. 23–24, the method of using the cement mold 110 to form a temporary femoral knee implant or prosthesis 150 will now be discussed. Initially, the bone cement and the antibiotic are again mixed to form an antibiotic impregnated bone cement 82 which is again loaded in the cement gun 72. An appropriately sized cement mold 110 is also selected. With the cement gun 72 loaded with the bone cement 82, the nozzle 70 is snugly received within the input port 140 with the first half 114 acting as the bottom portion of the mold and positioned on a table. This positioning of the cement mold 110 enables the vent holes 144 to be positioned at high points in the cement mold 110 to vent any trapped air as the cement 82 is delivered into the cement mold 110. Here again, the nozzle 70 may be directed within the input port 140 to direct the delivery of the bone cement 82 therein.

With the cement mold 110 being substantially transparent, a surgeon can determine when the cement mold 110 is substantially filled with the bone cement 82 as the mold is being vented by vents 144. Once the cement mold 110 is fully filled with the bone cement 82, the nozzle 70 is removed from the input port 140 and the mold 110 is left in this orientation until the cement 82 hardens and cures. Once hardened, a surgeon may simply cut along the medial plane 152 where the first half 114 is coupled to the second half 116 with a scalpel. Once scored or cut, the two halves of the mold 114 and 116 are then torn and separated to expose the temporary femoral knee implant 150. Alternatively, the first removal mechanism 98, as shown in FIG. 13, or the second removal mechanism 100, as shown in FIG. 14, may also be employed to provide a selectively tearable or removable area about a desired region. Tabs similar to the feet 32 of cement mold 10 may also be provided to assist in the removal of mold 110. Once the femoral prosthesis 150 is formed, it is engaged to the femur 154 to provide an anterior surface 156, a posterior surface 158 and condyles 160. Here again, it should be noted that the cement mold 110 will come pre-assembled and in a variety of sizes to accommodate the different shapes and needs of the patient.

Turning now to FIGS. 21–22, the cement mold 112 for use in forming a temporary tibial plateau is shown. The cement mold 112 includes a substantially planer outer base 162 and an outer circumferential sidewall 164. The tibia plateau implant is defined by an inner circumferential sidewall 166 and a base 168 having arcuate region 170 to form a mating surface with the two condyle regions 160 formed in the femoral knee implant 150. The cement mold 112 consists of a single unit and has its top substantially exposed.

Referring now to FIGS. 22 and 24, the method and procedure of employing the cement mold 112 to form the temporary tibial plateau 172 is shown. Here again, the proper mixture of bone cement and antibiotic is prepared and may either be inserted into to the cement gun 72 or left in an appropriate mixing bowl. Once mixed, the cement mold 112 is laid upon the outer base 162 exposing the upturned inner sidewall 166. The bone cement 82 is then delivered to the interior of the mold 112 either by way of the cement gun 72 or by merely pouring the bone cement 82 from the bowl into the cement mold 112. The thickness of the bone cement 82 may be matched with graduations 174 which appear on the inside of the base 162 in order to adjust the thickness depending on the patients needs. The graduations 174 are shown running about the inner circumference of the sidewall 166, but may only be on one portion of the sidewall 166.

Once the proper depth is selected, a plunger or paddle 176 having a handle 178 and a textured surface 180 is used to substantially shape the tibial plateau 172 and create a textured surface which will engage the tibia 182. By pressing and applying the plunger 178 which engages the inner sidewalls 166, trapped air within the bone cement 82 is released. Once the tibial plateau implant 172 is formed, the surgeon will let the mold 112 sit as the bone cement hardens and cures. Once hardened, the tibial plateau implant 172 is removed from the mold 112 by flexing or tearing the mold 112. The surgeon may then introduce antibiotic loaded bone cement 82 into any voids 184 formed within the tibia 182 by the first permanent implant. Once the voids 184 have been filled, the tibial plateau implant 172 is positioned textured side down on the tibia 182. The distended joint is then brought together to form a temporary articulating joint, as shown in FIG. 24. Here again, the implants 150 and 172 are not a load bearing implant but enable the distended joints to be brought together thereby enabling the patient to move in a limited matter.

Figure 25:
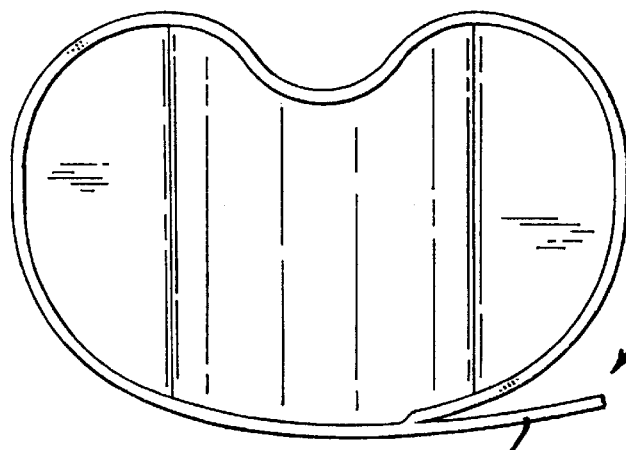
FIG. 25 is a top elevational view of the cement mold of FIG. 21 shown employing a third removal mechanism for removing the cement mold of FIG. 21.
Figure 26:
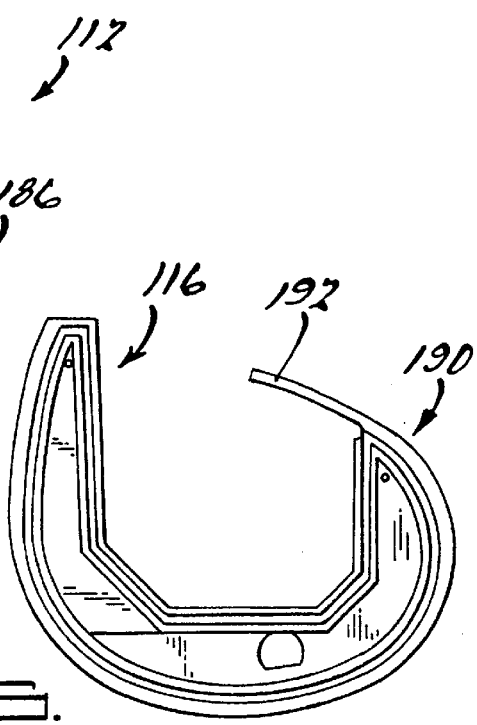
FIG. 26 is a side elevational view of a portion of the cement mold of FIG. 15 employing a fourth removal mechanism for removing the cement mold of FIG. 15.

Turning now to FIGS. 25–26, modified versions of the cement molds 112 and 110 are shown, respectively. In this regard, the cement mold 112 is shown with a third version of removal mechanism 186 having an extended pull tab 188 which may assist in removing the temporary tibial implant 172 by tearing the cement mold 112 about sidewall 164, thereby leaving only the base 162. The thinned member 104 may also be formed along the sidewall 164 adjacent to the base 162 to further enhance tearing about this circumference.

Referring to FIG. 26, the second half 116 of the cement mold 110 is shown with a fourth version of a removal mechanism 190 having a pull tab 192 extending from the posterior portion 120. The pull tab 192 also may be used to assist in tearing away the disposable cement mold 110.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A cement mold to form a temporary implant for use in delivering antibiotics to an infected site, said cement mold comprising:
    a first mold operable to define a first portion of the temporary implant;
    a second mold operable to define a second portion of the temporary implant;
    a coupling mechanism operable to join said first mold to said second mold such that upon joining said first mold with said second mold, said cement mold is substantially sealed to define the temporary implant;
    a removal mechanism operable to assist in rearing and separating said cement mold from the temporary implant, said removal mechanism including a pull string that is operable to assist in tearing and separating said cement mold from the temporary implant; and
    a foot attached to said cement mold, said foot operable to enable said cement mold to sit upon a flat surface.

2. The cement mold as defined in claim 1 wherein said cement mold further defines an input port, said input port operable to sealably receive a delivery nozzle.

3. The cement mold as defined in claim 2 wherein said cement mold further defines at least one ventilation port, said ventilation port operable to vent trapped air upon filling said cement mold with antibiotic loaded bone cement through said input port.

4. The cement mold as defined in claim 1 wherein said cement mold forms a femoral hip implant having a head, a neck and a distal stem.

5. A cement mold to form a temporary femoral implant for use in delivering antibiotics to an infected site, said cement mold comprising:
    a first mold operable to define a first portion of the temporary femoral implant;
    a second mold operable to define a second portion of the temporary femoral implant;
    a coupling mechanism operable to join said first mold to said second mold such that upon joining said first mold with said second mold, said cement mold is substantially sealed to define the temporary femoral implant; and
    a foot attached to a head portion of said cement mold operable to enable said cement mold to sit upon a flat surface.

6. A cement mold to form a temporary implant for use in delivering antibiotics to an infected site, said cement mold comprising:
    a first mold operable to define a first portion of the temporary implant;
    a second mold operable to define a second portion of the temporary implant;
    a coupling mechanism operable to join said first mold to said second mold such that upon joining said first mold with said second mold, said cement mold is substantially sealed to define the temporary implant; and
    a foot defining a cutout region operable to assist in separating said first mold from said second mold.

7. The cement mold as defined in claim 1 wherein said cement mold forms a temporary femoral knee implant.

8. The cement mold as defined in claim 1 where in said coupling mechanism includes a groove in said first mold and a tongue in said second mold.

9. The cement mold as defined in claim 8 wherein said tongue and groove defines a ventilation port passing therethrough.

10. The cement mold as defined in claim 5 further comprising a removal mechanism operable to assist in tearing and separating said cement mold from the temporary implant.

11. The cement mold as defined in claim 10 wherein said removal mechanism is selected from a group consisting of a thin member, a pull string, a tongue and groove connection, and a pull tab.

12. The cement mold as defined in claim 1 wherein said first mold and said second mold are formed from a semi-transparent material.

13. The cement mold as defined in claim 4 wherein said neck of said femoral hip implant has an enlarged cross-sectional area.

14. A cement mold to form a temporary implant for use in delivering antibiotics to an infected site, said cement mold comprising:
    an outer sidewall and an inner sidewall, said inner sidewall operable to define a shape of the temporary implant;
    an input port defined by said cement mold, said input port operable to receive a delivery nozzle to supply antibiotic loaded bone cement within said inner sidewall;
    at least one ventilation port defined by said cement mold, said ventilation port operable to vent trapped air upon filling said cement mold with the antibiotic loaded bone cement through said input port; and
    a foot attached to said cement mold, said foot operable to enable said cement mold to sit upon a flat surface.

15. The cement mold as defined in claim 14 wherein said cement mold further includes a removal mechanism operable to assist in removal of said cement mold from the temporary implant.

16. The cement mold as defined in claim 15 wherein said coupling mechanism includes a groove in said first mold and a tongue in second mold.

17. The cement mold as defined in claim 15 wherein said removal mechanism is selected from a group consisting of a thin member, a pull string, a tongue and groove connection, and a pull tab.

18. The cement mold as defined in claim 14 wherein said inner sidewall is operable to define a shape of the temporary implant selected from a group consisting of a femoral hip implant and a femoral knee implant.

19. A cement mold to form a temporary implant for use in delivering antibiotics to an infected site, said cement mold comprising:

an outer sidewall and an inner sidewall, said inner sidewall operable to substantially define a shape of the temporary implant;

a removal mechanism operable to assist in separating said cement mold from the temporary implant; and a plunger having a textured surface to define a textured surface on a portion of the temporary implant.

20. The cement mold as defined in claim 19 wherein said removal mechanism is selected from a group consisting of a thin member, a pull string, a tongue and groove connection, and a pull tab.

21. The cement mold as defined in claim 19 wherein said inner sidewall is operable to substantially define a shape of a tibial knee implant.

* * * * *